United States Patent [19]

Sutter

[11] Patent Number: 4,846,567
[45] Date of Patent: Jul. 11, 1989

[54] RETINAL AREA RESPONSE MAPPING USING SIMULTANEOUS MULTI-AREA STIMULATION WITH BINARY SEQUENCES AND OBJECTIVE RESPONSE ANALYSIS

[76] Inventor: Erich E. Sutter, 213 Hillsdale Way, Redwood City, Calif. 94062

[21] Appl. No.: 893,789

[22] Filed: Aug. 6, 1986

[51] Int. Cl.⁴ .............................................. A61B 3/00
[52] U.S. Cl. .................................. 351/224; 351/246; 128/745
[58] Field of Search ............... 351/205, 222, 223, 237, 351/239, 224, 225, 226, 246; 128/745

[56] References Cited

U.S. PATENT DOCUMENTS

| | | | |
|---|---|---|---|
| 3,883,235 | 5/1975 | Lynn et al. | 351/246 |
| 4,131,113 | 12/1978 | Fender et al. | 128/745 |
| 4,255,023 | 3/1981 | House | 351/226 |
| 4,676,611 | 6/1987 | Nelson et al. | 351/205 |

FOREIGN PATENT DOCUMENTS

0199218  10/1986  European Pat. Off. ............ 351/237

Primary Examiner—Rodney B. Bovernick
Assistant Examiner—J. P. Ryan
Attorney, Agent, or Firm—David Pressman

[57] ABSTRACT

Visual disorders of the retina are identified and assessed by stimulating the eye(s) with an array of controllable optical elements wherein the controllable elements are activated with M-sequences. The transient responses of the eye to the activation of the array of elements is obtained and processed using the known M-sequences to identify any areas of disease. The optically controllable elements can produce flashes of light or change colors in response to the energization thereof.

18 Claims, 8 Drawing Sheets

Fig. 2c m-sequence
(channel 1)

response
contributions
of the
individual
input
chanels

*Extraction of response contribution 3 from the overall response* overall
response input
sequence of
channel 3 average of
products over
the 7 time bins

*Verification: Consider each response contribution separately* products of
input
sequence 3
with the
response
contributions averages of
products over
the 7 time bins

RETINAL AREA RESPONSE MAPPING USING SIMULTANEOUS MULTI-AREA STIMULATION WITH BINARY SEQUENCES AND OBJECTIVE RESPONSE ANALYSIS

The U.S. government has rights in the claimed invention pursuant to NIH Grant No. EYO-6861.

BACKGROUND OF THE INVENTION

This invention relates generally to the diagnosis and assessment of treatment of visual disorders by objective means. More specifically it relates to the determination of extent and magnitude of local defects in the visual field of the eye by simultaneous stimulation of a large number of locations on the retina and analysis of the elicited electrical signals derived from the eye (electroretinogram or ERG) or the scalp (visual evoked cortical response or VECR).

Most pathologies of the human visual system do not affect the entire visual field equally, but begin in small patches which then may grow into larger field defects. The locations of those patches on the retina are often a characteristic of the disease. The detection and determination of the size of such defects is thus of great importance not only for diagnosis, but also for the assessment of treatment. The techniques currently used in the clinic for this purpose are psychophysical in nature i.e., they require a judgement and response from the patient. They are thus subjective and often difficult to use, especially with very young or old patients, or persons who for other reasons are unable to adequately perform the task. The most popular techniques for retinal "mapping" or debut location determinates are known under the names "tangent screen" or "perimetry". More or less automated equipment for performing perimetry is commercially available from companies such as Goldman, Baush and Lomb, Coopervision, and others. The process of obtaining visual field plots with such equipment is usually lengthy, laborious (if not for the operator then always for the patient) and produces results which are not always reliable. Objective bioelectrical signals are currently obtained and used in the clinic, to obtain global responses from the entire visual field or a large segment thereof. The usefulness of smaller stimuli (focal ERG and VECR) has been demonstrated most notably by Sandberg and Berson and by Hirose et al. However, the techniques introduced by these authors only permit testing of one location at a time. Application of their technique for the purpose of objective perimetry was heretofore thought not feasible for two reasons: sequential testing of a large number of retinal location is much too time consuming for clinical applications, and comparison of signals obtained sequentially from different locations is unreliable because of temporal variations in signal-to-noise ratio. A different approach has recently been presented at the annual meeting of the Association for Research in Vision and Opthamology (ARVO). In the approach, each location of the retina is stimulated with a signal of a different frequency. However this imposes theoretical as well as practical limitations on the number of locations which can be simultaneously tested. While these investigators hope to be able to test up to 64 locations, they are currently testing only 8 or 16 locations.

The present invention overcomes those limitations by the simultaneous stimulation of a large number of locations. Acceptable results are obtained in times feasible in the clinic (10 to 20 minutes) and artifactual noise, such as produced by blinks, affects all focal responses the same or to a similar degree.

In carrying out the invention a matrix of independently controllable optical elements is placed in the field of view of the patient. A special class of binary sequences, called M-sequences, is utilized in electronically activating the elements. M-sequences are discussed in Golomb, *Shift Register Sequences*, 1982, Aegean Park Press, Laguna Hills, Calif.

The present invention permits the testing of a much larger number of locations. Currently 256 are used, but an increase to 2000 or more is feasible without extending the length of the procedure.

Various types of focal stimulation can be used with the present invention such as local flash and local pattern reversal color alternation. The most appropriate mode of stimulation depends on the pathology at hand.

The invention and objects and features thereof will be more readily apparent from the following detailed description and appended claims when taken with the drawings, in which:

DETAILED DESCRIPTION OF THE ILLUSTRATIVE EMBODIMENT

Figure 1:
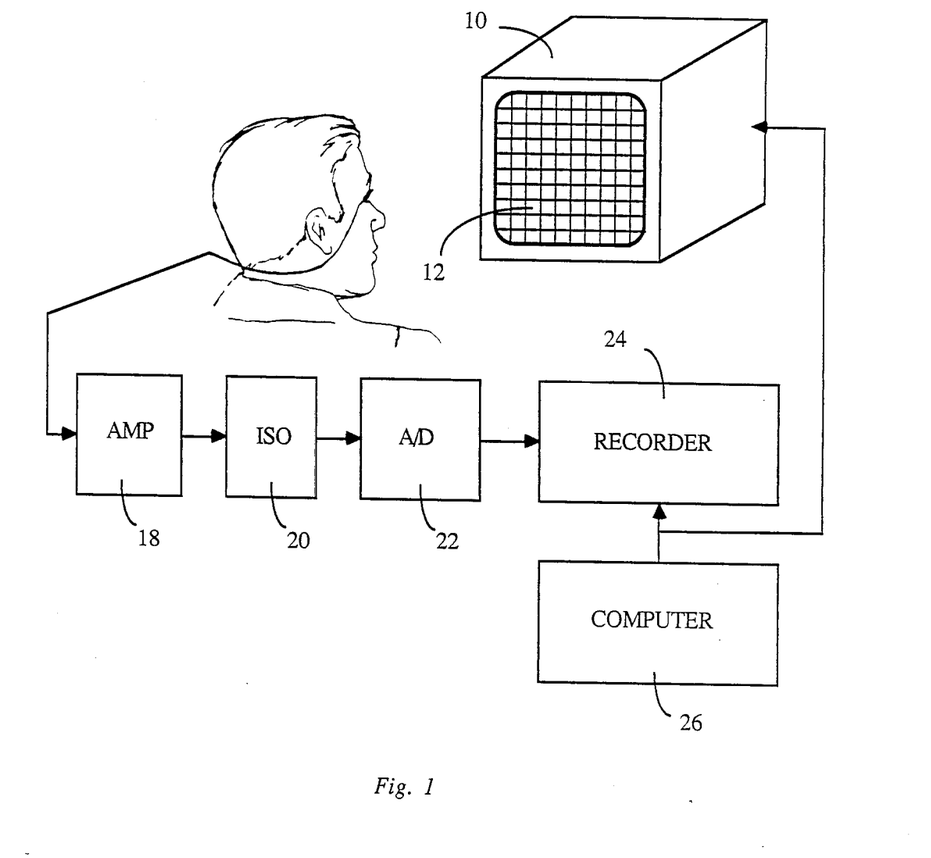
FIG. 1 is functional block diagram of a perimetry system which can perform objective analysis using measured evoked potentials in accordance with the invention.

Referring now to the drawings, FIG. 1 is a functional block diagram of a perimetry system which can perform objective analysis using measured evoked potential in accordance with the invention. A display 10 having a plurality of independently controlled optical elements 12 is provided for visual stimulation of a patient 14. In this embodiment the visual display comprises a color CRT display and the independently controlled optical elements comprise a matrix of 256 elements which can be temporally modulated in their luminance, color or pattern presented on each field. A standard clinical ERG (or VECR resp.) electrode pair 16 is placed on the eyeball (or scalp) of the patient. The signal from electrode pair 16 is amplified at 18, passed through an optical isolator 20 for patient safety, converted from analog to digital form by an A/D converter 22, and recorded at 24. The signal aquisition components are conventional in obtaining ERG or VECR signals.

A computer 26 generates the temporal modulation of the optical elements 12. In synchrony with the stimulus modulation, it also acquires the sampled ERG (or VECR) signal for later processing.

Each optical element is modulated according to the same binary M-sequence cycle. However the starting times for the respective elements are equally distributed on the cycle. Thus if there are 256 elements the stimulation sequence is delayed by 1/256th of a cycle from one element to the next.

After the recording has been completed the response contributions from each optical element are computed by means of a simple cross-correlation algorithm. The computed response waveforms associated with the elements can be directly interpreted or a gray scale plot can be derived which represents the stimulus matrix, whereby the brightness of the elements is indicative of the response amplitude for that location.

Figure 2A:
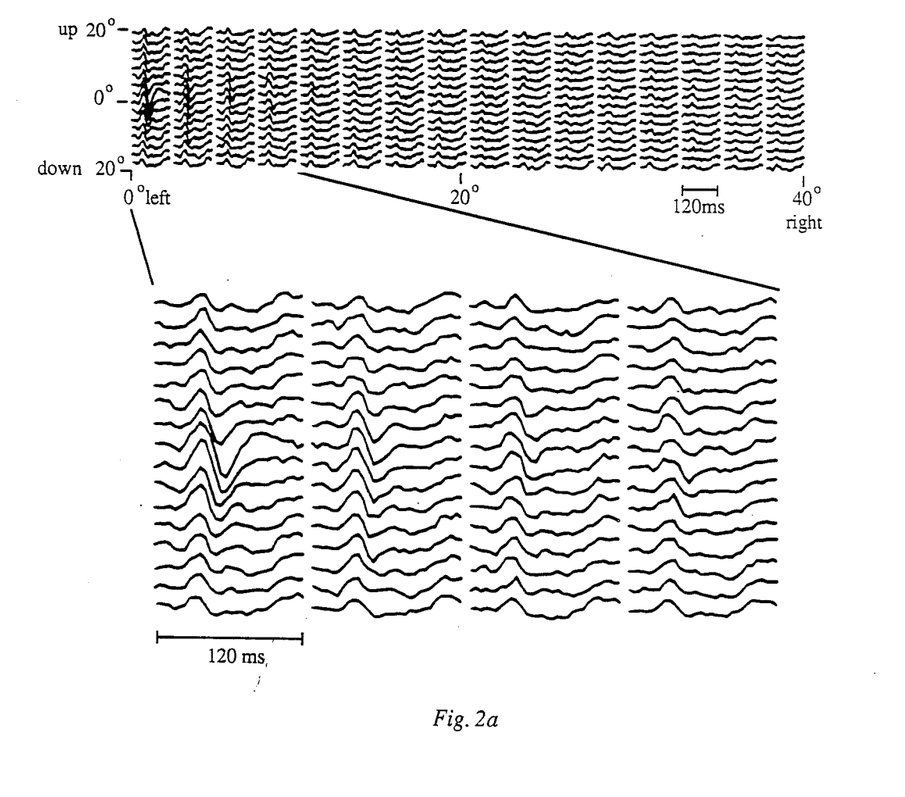
FIG. 2A shows the waveforms derived from 256 locations of a healthy retina by means of ERG perimetry.
Figure 2B:
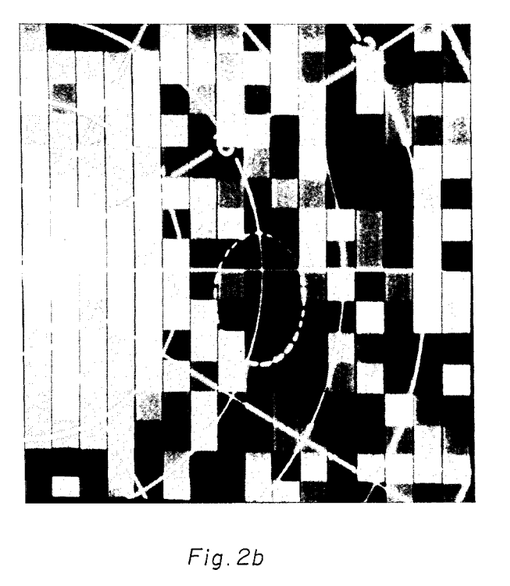
FIGS. 2B and 2C are Gray scale plots for a normal retina and a diseased retina (big blind spot syndrome), respectively.
Figure 2C:
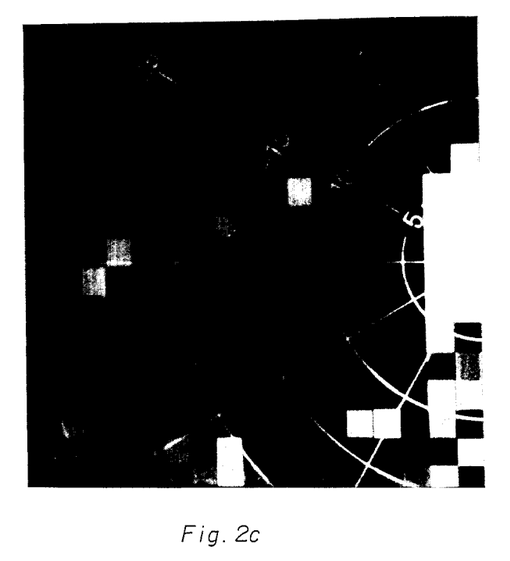

Results from these types of data processing are shown in FIGS. 2A to 2C. The top waveform traces of FIG. 2A show an array of 256 ERG responses and, as indicated by the divergent projection lines, the bottom waveforms are enlarged versions of the first four columns of these waveforms. Each trace represents the response generated by the corresponding optical element in the display matrix. The axes are labeled with the horizontal and vertical visual angles of the display measured from the fixation point. The increase in response amplitude toward the fixation point parallels the increase in cone type of visual receptor cells) densities in the central human retina.

FIG. 2b is gray scale representation of the response amplitudes for a normal eye. Here the signal amplitude corresponding to each location has been used to calculate the brightness of the corresponding square on FIG. 2b. The polar coordinates overlaid on the photograph measure eccentricity from the fixation point at the right display boundary. The dark, unresponsive area marked by the broken line is the blind spot where the optic nerve head is located.

FIG. 2c is a gray scale plot of the same retinal area of a patient suffering from big blind spot syndrome. The central response (area at zero coordinates) appears normal which is consistent with the measured normal visual acuity. However, the area surrounding the blind spot (area surrounded by broken oval) is largely unresponsive except for isolated patches.

Figure 3:
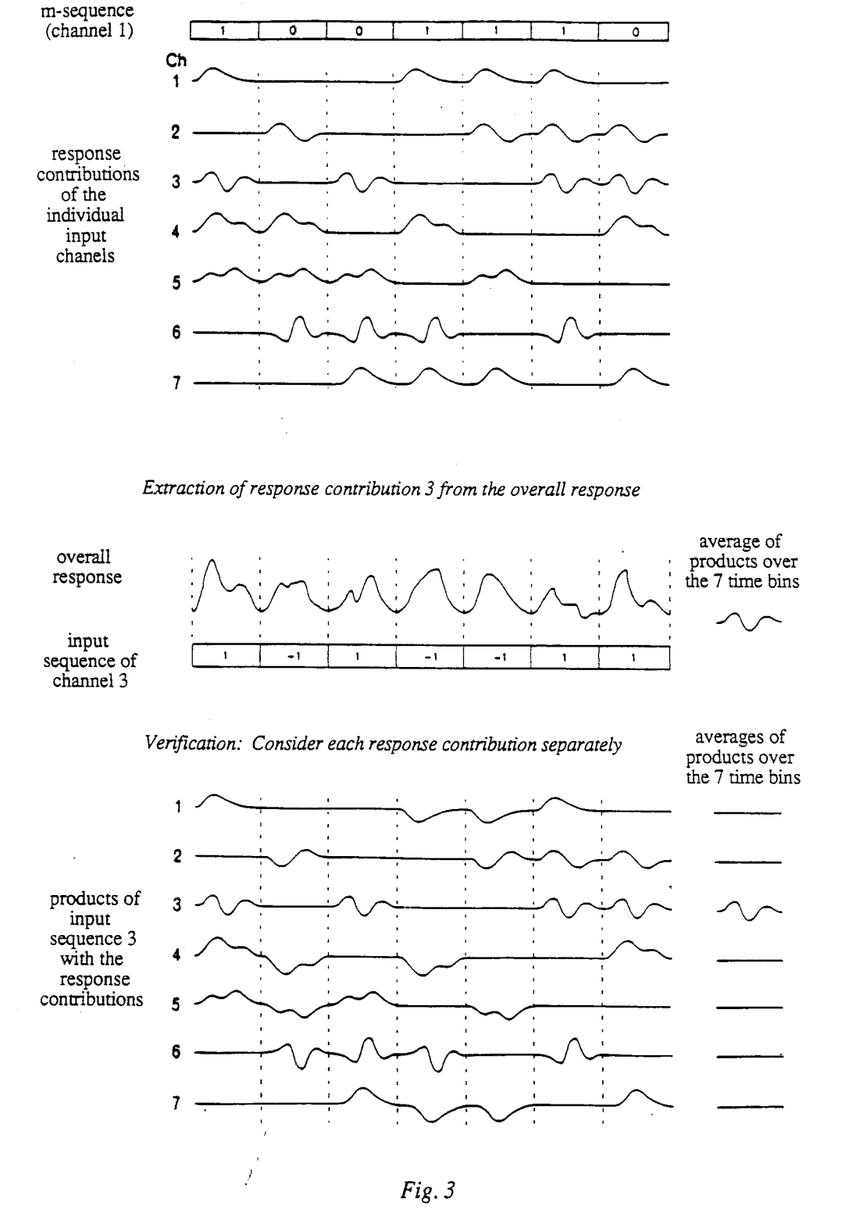
FIG. 3 illustrates simultaneous stimulation of seven input channels with a sequence of pulses.

The primary goal of the recording technique is the derivation of an impulse response for every position in a two dimensional array of retinal stimulus locations. The method is based on the concept of the transient response, i.e., the response to a discrete stimulus event such as a flash. Instead of sequential presentation of flashes at each stimulus location, half of the locations are flashed at once. In the most basic form of the technique, the time interval between such flashes is chosen to be large enough to accommodate the response duration. In each such time interval, the flashed locations are selected differently such that after a certain number of flashes the contribution from each location can be computed. The flash sequence is periodic and the minimum number of flashes in the cycle is equal to the number of stimulus locations. FIG. 3 illustrates the basic technique using a simple example of seven input channels. All seven input channels are flashed according to the same binary cycle which determines whether or not the stimulus element is flashed. From one channel to the next this cycle is delayed by one step. The binary sequence for channel 1 is shown at the top of FIG. 3. The seven traces below represent the contributions of the seven channels to the overall response. The recorded output signal which, in the absence of interaction terms, is the sum of all these contributions, is shown in the center of the figure. A simple procedure permits extraction of the impulse response of any of the input channel from this signal. It is illustrated in the bottom half of the figure for channel 3. The response signal is multiplied with 1 in all those time intervals where channel 3 was flashed and with $-1$ in all the others. Subsequent averaging of the seven segments of the resulting time series yields the impulse response of channel 3. The seven traces at the bottom of the figure show that the contribution from all the other input channels cancel out through this procedure.

The computed impulse responses are in each case averages of four flash responses. A test of the same duration by means of the standard method of sequential testing produces only one response. Thus, a twofold increase in signal-to-noise ratio can be expected. The comparison becomes more favorable as the number of input channels increases. With 255 inputs, each channel is flashed 128 times during a cycle and the improvement in signal-to-noise ratio is thus better than eleven-fold.

This technique is made possible by special properties of the binary sequence which defines the stimulus cycle. Binary M-sequences have these properties. They always have a cycle length of $2^n - 1$ elements where n is an integer.

In order to further improve the signal-to-noise ratio it may be desirable to increase the stimulus power by reduction of the basic time interval beyond the point where the responses to consecutive flashes start to overlap. Consider, for example, a simple doubling of the flash rate. The basic interval is now half the response duration. The time intervals to be multiplied and averaged in the extraction procedure described above are now doubled in size and overlap with each other. The second half of each such interval is thus multiplied with the sequence corresponding to the next channel. After averaging it will not only contain the end of the impulse response, but will also contain superimposed on it the beginning of the next channel. This overlap can be avoided if the stimulation sequences of consecutive channels are relatively delayed by two steps of the binary sequence rather than one. To accommodate the same number of input channels the length of the M-sequence has to be doubled.

If desired, the flash rate can be increased further, as long as the relative delay T between the input sequences of consecutive channels is equal to or larger than the response duration and the stimulus cycle is equal to or longer than $T*k$, where k is the number of channels.

By increasing the flash rate simultaneously with k towards the high frequency cutoff of the system, one arrives in a smooth transition at the well-known binary white noise analysis.

M-sequence stimuli have a flat temporal spectrum down to very low frequencies where the ERG and VECR responses are poor. The efficiency of the technique can be further enhanced, if stimulus power could be shifted from the low frequency and into the region of maximal response. This can be accomplished by means of a simple modification of the flash sequence.

For example, instead of flashing the inputs only in those time intervals where the M-sequence element is a 1, each input is now flashed in every interval. The modulation is now produced by the timing of the flash. The flash occurs at the beginning of those intervals where the M-sequence element is a ONE, an at the center, i.e., delayed by an interval T/2, of those intervals where the M-sequence element is a ZERO. The resulting stimulus sequence has a frequency peak near 1/T. The amplitude drops off linearly and the power quadratically towards the low frequency end.

Figure 4:
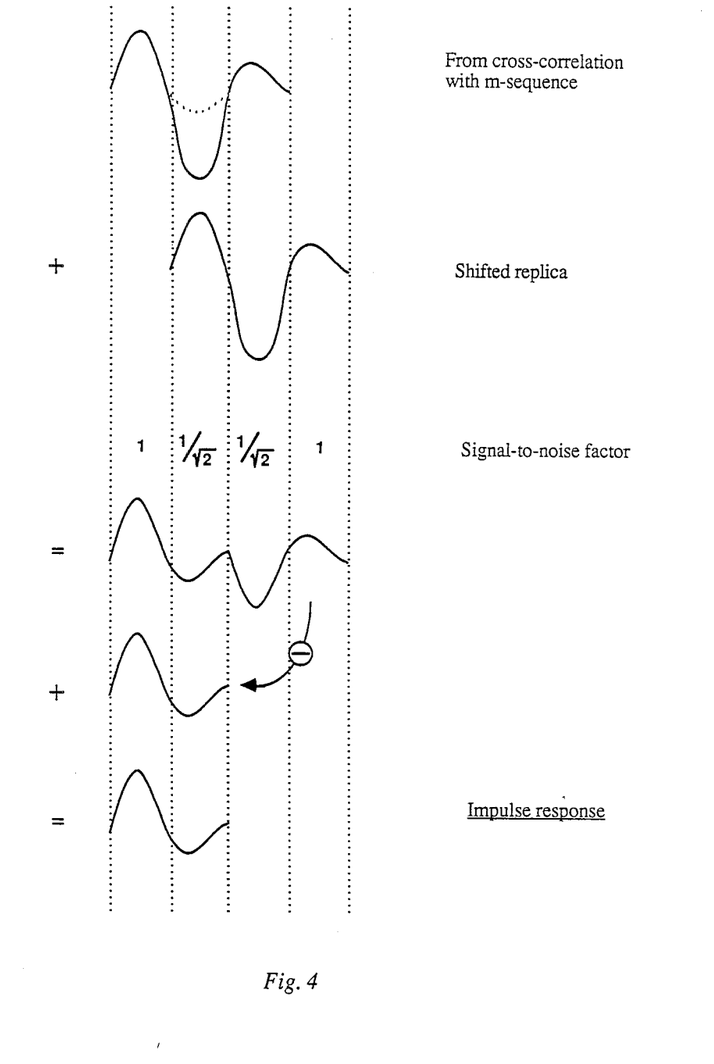
FIG. 4 illustrates retrieval of an actual impulse response in accordance with one embodiment of the invention.

The analysis described in FIG. 3 now yields the sum of two relatively inverted impulse responses. The second one, also being delayed by T/2, is contributed by the intervals associated with M-sequence ZEROS. If T is chosen equal to the period of the dominant response frequence, the amplitudes of the two impulse responses add over most of the response duration as shown in the top trace of FIG. 4. The actual impulse response can be retrieved by means of the simple technique illustrated step by step in FIG. 4:

a. Zero the segments immediately preceding and following the response.

b. Add the response to itself with a delay T/2. The inverted second impulse response now appears delayed by T.

c. The two separated impulse responses can now be added with proper sign for better signal-to-noise ratio. Since the two responses have different signal-to-noise ratios in their first and second halves, they should be added with corresponding weights.

If the impulse response is larger than t, separation requires repetition of step b. with relative delays of t, 2t, etc.

A complication arises from the fact that ERG and VECR responses are not linear. Signals originating from different inputs do not simply superimpose, but interact with each other. In other words, different input channels affect each other's response. In the case where discrete flash inputs are used, this effect can be estimated by subtraction of the signal intervals where both inputs in question were the same (flashed or not flashed) from those where only one was flashed. Consulting FIG. 3 we easily verify that the 1 and −1 multipliers for the interaction term between channel 1 and 2 are identical to those for extraction of the impulse response of channel 4. This interaction term will thus appear superimposed on the average impulse response of channel 4. In fact, the interaction terms between any pair is superimposed on one of the averaged impulse responses. They can, however, be separated out by means of a well-known 'inverse repeat' trick. The same experiment is performed a second time but with the inverse stimulation sequence (flashed and non-flashed intervals are interchanged). Subtraction of the second data set from the first isolates the impulse responses; addition isolates the pair interactions.

In the example of FIG. 3 there are 21 possible pair interactions, but the M-sequence has only length 7. Three interaction terms must thus always be superimposed on one another. It is not always necessary to use longer M-sequences to isolate the terms. In the case of VECR and ERG responses, the only interactions of significance are those between neighboring stimulus elements. With a linear stimulus array the number of neighboring pairs is no larger than the number of array elements, i.e., all important pair interactions are well separated. In a two dimensional array of stimulus squares where horizontal and vertical neighbors interact, their respective contributions can be isolated by a modified version of the inverse repeat trick. In a second set of experiments every second row is inverted. Addition of the data from the two sets will isolate the interactions between horizontal neighbors, and subtraction will isolate that of the vertical pairs.

When the flash rate is increased as described above, interactions may occur not only between simultaneous flashes of different input channels, but also between consecutive flashes of the same as well as different inputs. The number of possible interaction terms increases very rapidly, and increasingly longer M-sequences are needed for their isolation. Usually the required recording times become prohibitively long before the analysis approaches the criteria for white noise analysis.

Figure 5:
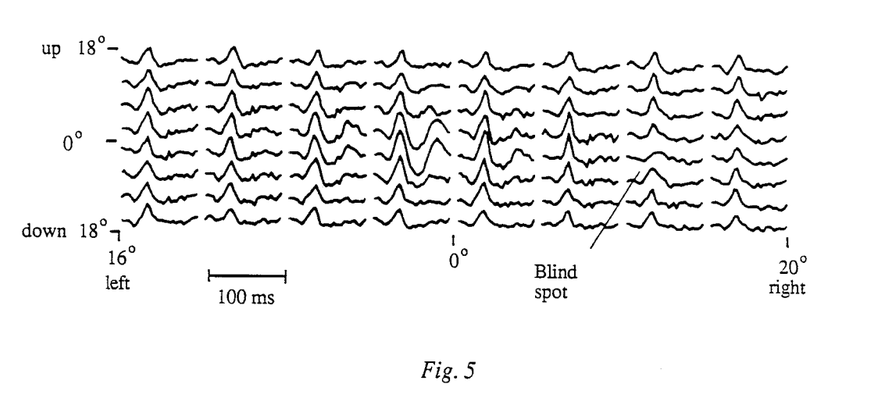
FIG. 5 illustrates computed average ERG impulse responses for a stimulus matrix of 8×8 squares in a 32° by 32° field.

The data presented in FIGS. 5 and 2a are ERG data actually obtained with an 8×8 and 16×16 element stimulus matrix of small squares. Burian-Allen electrodes were used to derive the signal from the eyeball. Every trace represents the average impulse response of the corresponding stimulus location. In both cases the net recording time was less than 15 minutes. The data were accumulated in 40 second segments. The flash rate (frame rate) was 40 per second. The inverse repeat technique was used to eliminate the major interaction terms. The length of the M-sequence in both experiments was $2^{16}-1$ elements. No rejection of blink or movement artifacts was used.

These photopic responses show a slow decrease with eccentricity which parallels changes in cone density. The data demonstrate that the local retinal response can be tested with relatively high spatial resolution in recording times of tolerable length.

Figure 6:
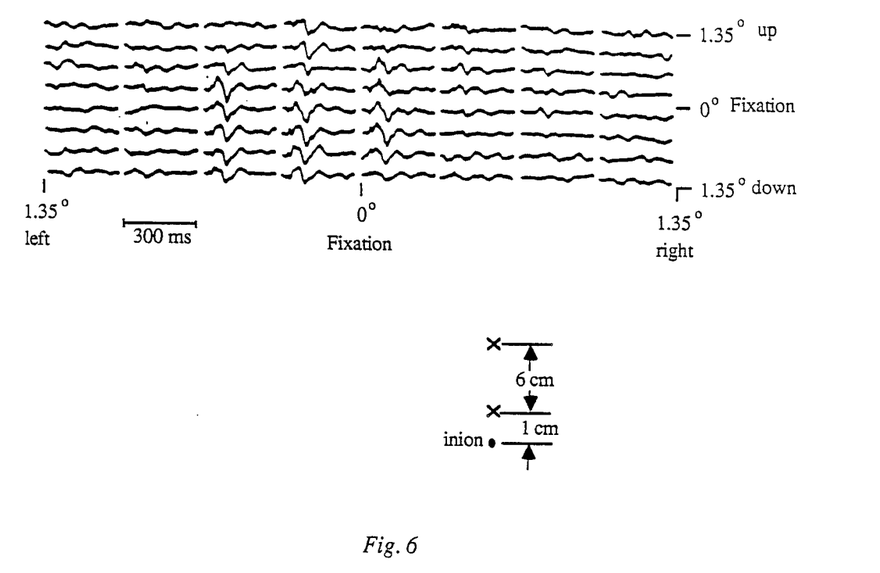
FIG. 6 illustrates computed average VER impulse responses for a stimulus matrix of 8×8 squares in a 2.7°×2.7° field.
Figure 7:
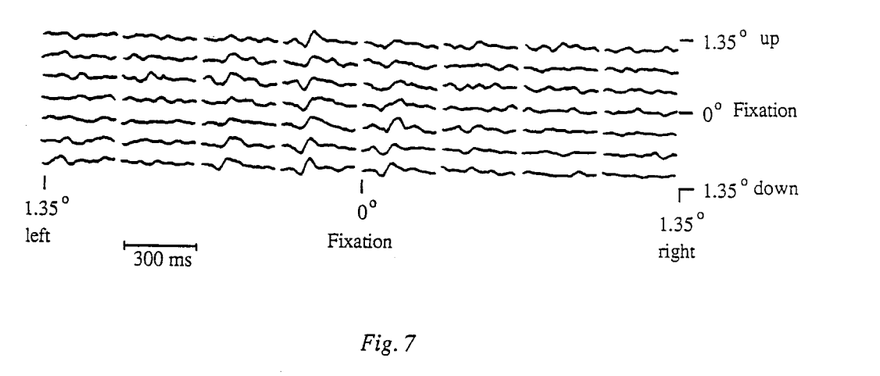
FIG. 7 illustrates interactions between simultaneous flashes of vertically adjacent squares obtained from the record of FIG. 7.

FIG. 6 shows local VER responses recorded with a differential electrode pair placed as shown to the lower right. An 8×8 stimulus matrix was used to simulate the central 2.7×2.7 degrees of the visual field. The frame rate was 25 per second. The inverse repeat technique was used to isolate these average responses from the interaction terms. FIG. 7 shows the interactions between simultaneous flashes of vertically adjacent elements.

Figure 8:
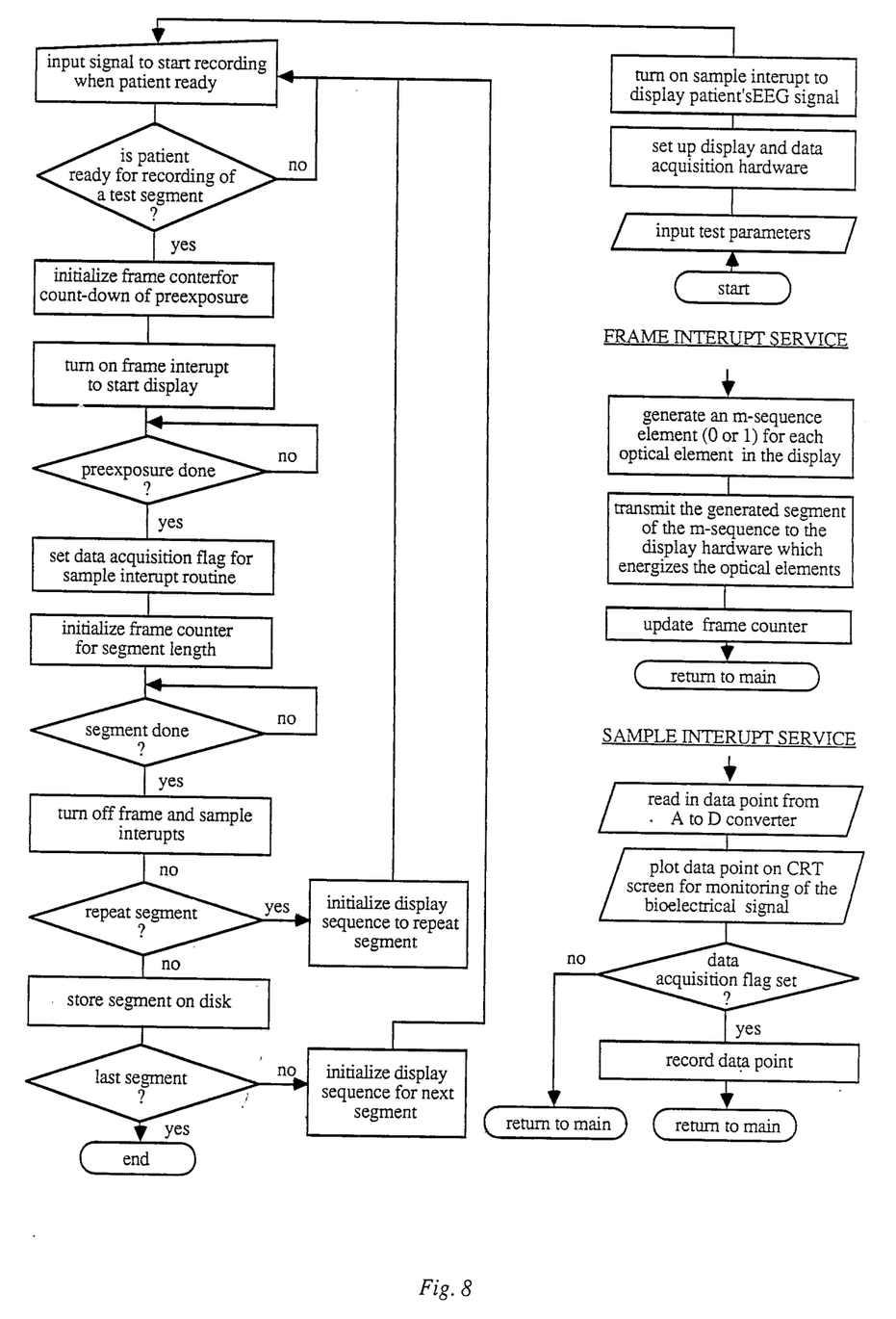
FIG. 8 is a flow diagram of a program for recording the measured responses using the known M sequence to identify diseased spots of the retina.

FIG. 8 is a flow diagram of a program for recording the measured responses of the retina in response to the M-sequence control of the visual display. An entire M-sequence stimulus cycle has to be recorded (each optical element is activated according to the entire M-sequence). This is necessary to guarantee the best signal-to-noise ratio and complete isolation of the response contributions from the different optical elements in the subsequent data processing. The record is obtained in segments of approximately 20 to 40 seconds in length with breaks in between for the comfort of the patient. With each segment stimulation is started one or two seconds before recording begins (preexposure), in order to avoid the transient generated by the stimulus onset and to guarantee that at the time recording begins the signal is valid. The refresh of display frames and the sampling of the bioelectrical signals are interrupt driven. Several samples can be recorded between frame refresh. The interrupts (frame and sample interrupt) are generated by the display and data acquisition hardware. The corresponding interrupt service routines are charted separately.

Figure 9:
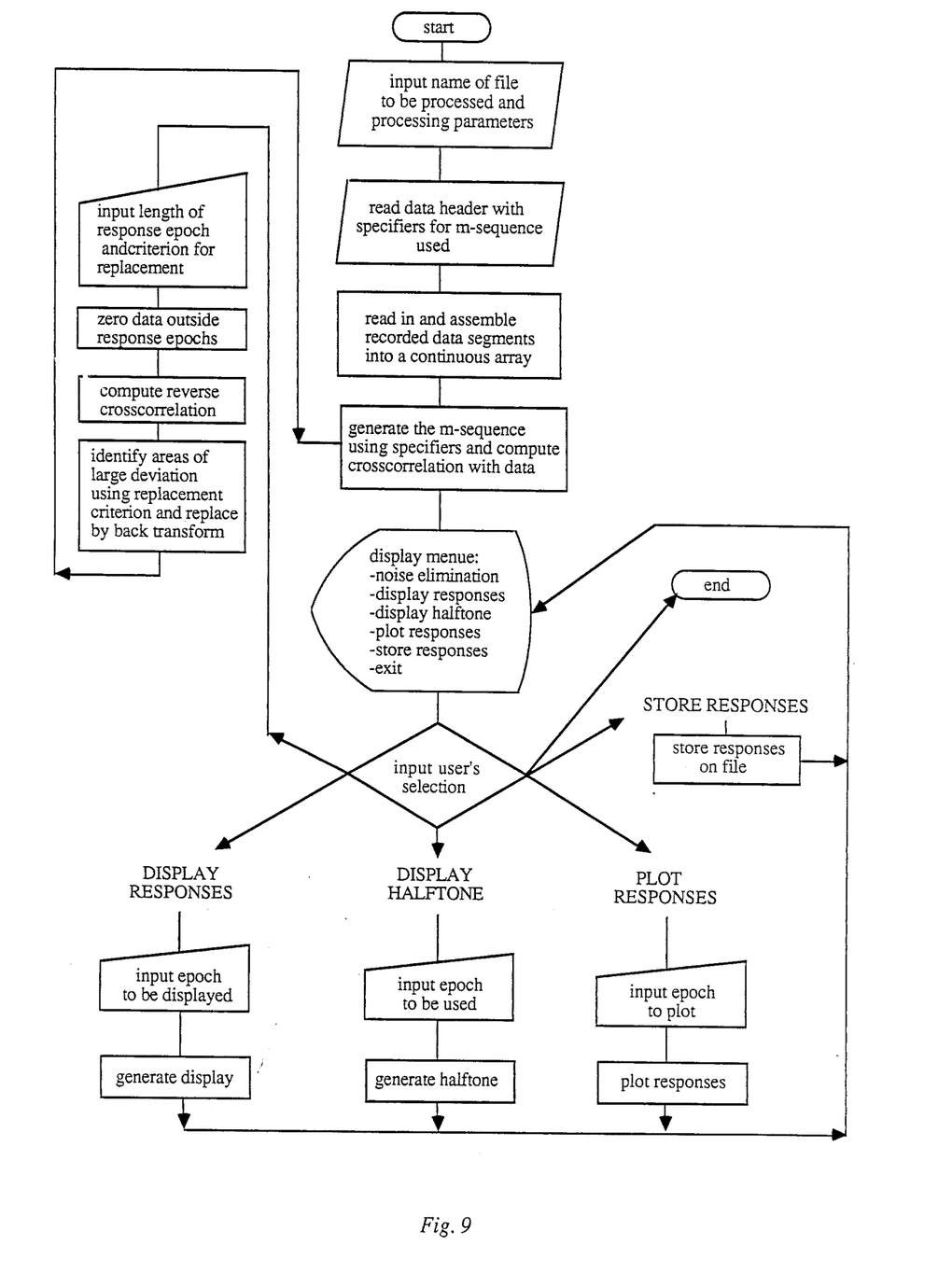
FIG. 9 is a flow diagram of a program for processing the recorded responses.

FIG. 9 is a flow diagram of a program for processing the recorded responses. Data processing consists of a cross-correlation of the time series recorded with the recording program with a series derived from the M-sequence used for stimulation. To generate the latter all the zeros, M-sequence are replaced by ones, and all elements are then separated by $k-1$ zeros where k is the number of data points recorded per display frame. The resulting series cross-correlation is cyclical as both the input and the output series are cycles with no beginning and no end. Equally distributed on the resulting cross-correlation cycle appear the responses for each of the independently-stimulated retinal locations. If nonlinearities are negligible, as e.g. with the flash ERG, these represent the focal impulse responses. The focal responses are separated on the cross-correlation cycle by stretches of noise which is largely due to artifacts from blinks and other movement. Even though these artifacts are relatively rare events in the original data, they distribute their energy over the cross-correlation cycle, contaminating the responses as well as the space in between. If it is known that the space between the responses is almost exclusively filled with noise, this knowledge can be used to reduce the effect of the blink and muscle artifacts. This can be done as follows.

The space on the cross-correlation cycle between the responses is set to zero and the cycle is transformed back by means of the reverse cross-correlation. The resulting signal is then compared with the original data. The largest deviations indicate the locations of the artifacts. At these locations the data are now replaced by the back-transformed signal. Cross-correlation of the corrected data yields focal responses with reduced noise. This process can be iterated for best results. Note that once the length of the response epochs is specified, the segments between the epochs need not be computed in the cross-correlation since they will be set to zero. In the back transform, the points with zero amplitude do not contribute, i.e., these segments do not have to enter into the computation. Instead of setting them to zero, one can thus simply skip the segments. This results in considerable savings in computation time.

The focal responses can either be plotted as an array of waveforms if local variations in the response structure are of importance, or a single number can be derived from each waveforms which indicates the focal response power or amplitude. In a halftone image of the array of optical stimulators, this number can be represented as the brightness of the corresponding element. The result is very similar to plots produced by automated perimeters and can be easily interpreted by the clinician.

There has been described an improved method for the diagnosis and assessment of treatment of the eye for visual disorders by objective means. While the invention has been described with reference to specific embodiments, the description is illustrative of the invention and is not to be construed as limiting the invention. Various modifications and applications may occur to those skilled in the art without departing from the true spirit and scope of the invention as defined by the appended claims and their legal equivalents.

What is claimed is:

1. A method of mapping the retina for visual defects, comprising:
   (a) providing a two-dimensional array of electronically activatable optical elements,
   (b) activating all of the optical elements of said array with respective predetermined binary M-sequences,
   (c) causing a subject to view said activated elements of said array so that said elements will visually stimulate the retina of said subject,
   (d) obtaining a bioelectrical response from said subject in response to such visual stimulation,
   (e) analysing said bioelectrical response by comparing it with said predetermined binary sequences and using the results of the comparison to create a response plot of said retina.

2. The method of claim 1 wherein said step of activating said array of elements causes said elements to provide sequential light flashes.

3. The method of claim 1 wherein said step of activating said array of elements causes said elements to provide sequentially different colors.

4. The method of claim 1 wherein said step of activating said array of elements causes each of said elements to produce a predetermined optical output selected from the class consisting of light and color changes.

5. The method of claim 1 wherein said step of activating said array of elements causes said elements to reverse a pattern displayed by said elements.

6. The method of claim 1 wherein said step of analysing said bioelectrical responses includes cross-correlating said responses with a time series derived from said M-sequences.

7. The method of claim 6, further including making a reverse cross-correlation of the cross-correlated transient responses, comparing the resulting signal from the reverse cross-correlation with the original bioelectrical responses, and identifying the artifacts due to deviations of said resulting signal from the original transient responses.

8. The method of claim 1 wherein said step of obtaining bioelectrical responses includes placing electrodes on the eyeball of a subject.

9. The method of claim 1 wherein said step of obtaining bioelectrical responses includes placing electrodes on the head of a subject.

10. The method of claim 1 wherein said step of activating said array of elements with respective predetermined binary sequences is performed with the same binary sequence for every element.

11. A system for creating a map of the retina for visual defects, comprising:
    (a) a two-dimensional array of electronically activatable optical elements,
    (b) means for activating all of the optical elements of said array with respective predetermined binary sequences,
    (c) means for obtaining a bioelectrical response of a subject to visual stimulation,
    (e) means for analysing said bioelectrical response by comparing it with said predetermined binary sequences and using the results of the comparison to create a retinal response plot.

12. The system of claim 11 wherein said means for activating said array of elements is arranged to activate said elements to produce light flashes.

13. The system of claim 11 wherein said means for activating said array of elements is arranged to activate said elements to cause said elements to change color.

14. The system of claim 11 wherein said means for activating said array of elements with respective predetermined binary sequences is arranged to activate every element with the same binary sequence.

15. The system of claim 11 wherein said means for activating said array of elements causes said elements to reverse a pattern displayed thereby.

16. The system of claim 11 wherein said means for analysing said bioelectrical responses includes means for cross-correlating said responses with a time series derived from said M-sequences.

17. The system of claim 16 wherein said means for analysing said bioelectrical responses includes means for making a reverse cross-correlation of the cross-correlated transient responses, and means for comparing the resulting signal from the reverse cross-correlation with the original transient responses, and means for identifying the artifacts resulting from deviations of said resulting signal from the original responses.

18. The system of claim 11 wherein said means for obtaining a bioelectrical response includes electrodes which can be placed on the body of a subject.

* * * * *

UNITED STATES PATENT AND TRADEMARK OFFICE
CERTIFICATE OF CORRECTION

PATENT NO. : 4,846,567

DATED : 1989 Jul 11

INVENTOR(S) : Sutter, E. E.

It is certified that error appears in the above-identified patent and that said Letters Patent is hereby corrected as shown below:

Col. 1, l. 34, change "determinates" to --determination--.

Col. 1, l. 42, start a new paragraph with "Objective".

Col. 1, l. 43, delete "," after "clinic".

Col. 1, after l. 65, insert the heading --SUMMARY--.

Col. 2, l. 16, after "invention" insert --,--.

Col. 2, l. 67, delete "resp."

Col. 3, l. 35, before "type" insert --(--.

Col. 3, l. 68, start a new paragraph with "FIG. 3".

Col. 4, l. 34, after "elements" insert --,--.

Col. 7, l. 4, change "," (first occurrence) to --of the--.

Col. 7, l. 9, start a new paragraph with "Equally".

Signed and Sealed this

Tenth Day of July, 1990

*Attest:*

HARRY F. MANBECK, JR.

*Attesting Officer*        *Commissioner of Patents and Trademarks*